United States Patent [19]
Wright

[11] Patent Number: 5,707,358
[45] Date of Patent: Jan. 13, 1998

[54] DUAL CONCENTRIC BALLOON CATHETER FOR RETROGRADE CARDIOPLEGIA PERFUSION

[76] Inventor: John T. M. Wright, 555 S. Downing St., Denver, Colo. 80209

[21] Appl. No.: 645,309

[22] Filed: May 13, 1996

[51] Int. Cl.⁶ .................................................. A61M 29/00
[52] U.S. Cl. ........................................ 604/96; 604/101
[58] Field of Search .................... 604/96, 100, 101, 604/102, 171, 264, 280, 283, 284, 53; 606/192, 194

[56] References Cited

U.S. PATENT DOCUMENTS

| | | | |
|---|---|---|---|
| 4,744,366 | 5/1988 | Jang | 128/344 |
| 4,994,033 | 2/1991 | Shockey et al. | 604/101 |
| 5,049,132 | 9/1991 | Shaffer et al. | 604/101 |
| 5,197,952 | 3/1993 | Marcadis et al. | 604/96 |
| 5,395,330 | 3/1995 | Marcadis et al. | 604/96 |
| 5,460,610 | 10/1995 | Don Michael | 604/101 |
| 5,569,184 | 10/1996 | Crockes et al. | 604/53 |

*Primary Examiner*—Corrine M. McDermott
*Assistant Examiner*—Cris L. Rodriguez

[57] ABSTRACT

A perfusion catheter for use in open heart surgery having inner and outer concentric balloons adjacent to the distal end of the catheter wherein the inner balloon is a cuff that may be inflated by a syringe using either air or liquid via a second lumen in the catheter, the outer balloon self-inflating when perfusion liquid flows through the catheter, and a third and lumen of the catheter to monitor the infusion pressure at the distal end of the catheter, is disclosed.

7 Claims, 2 Drawing Sheets

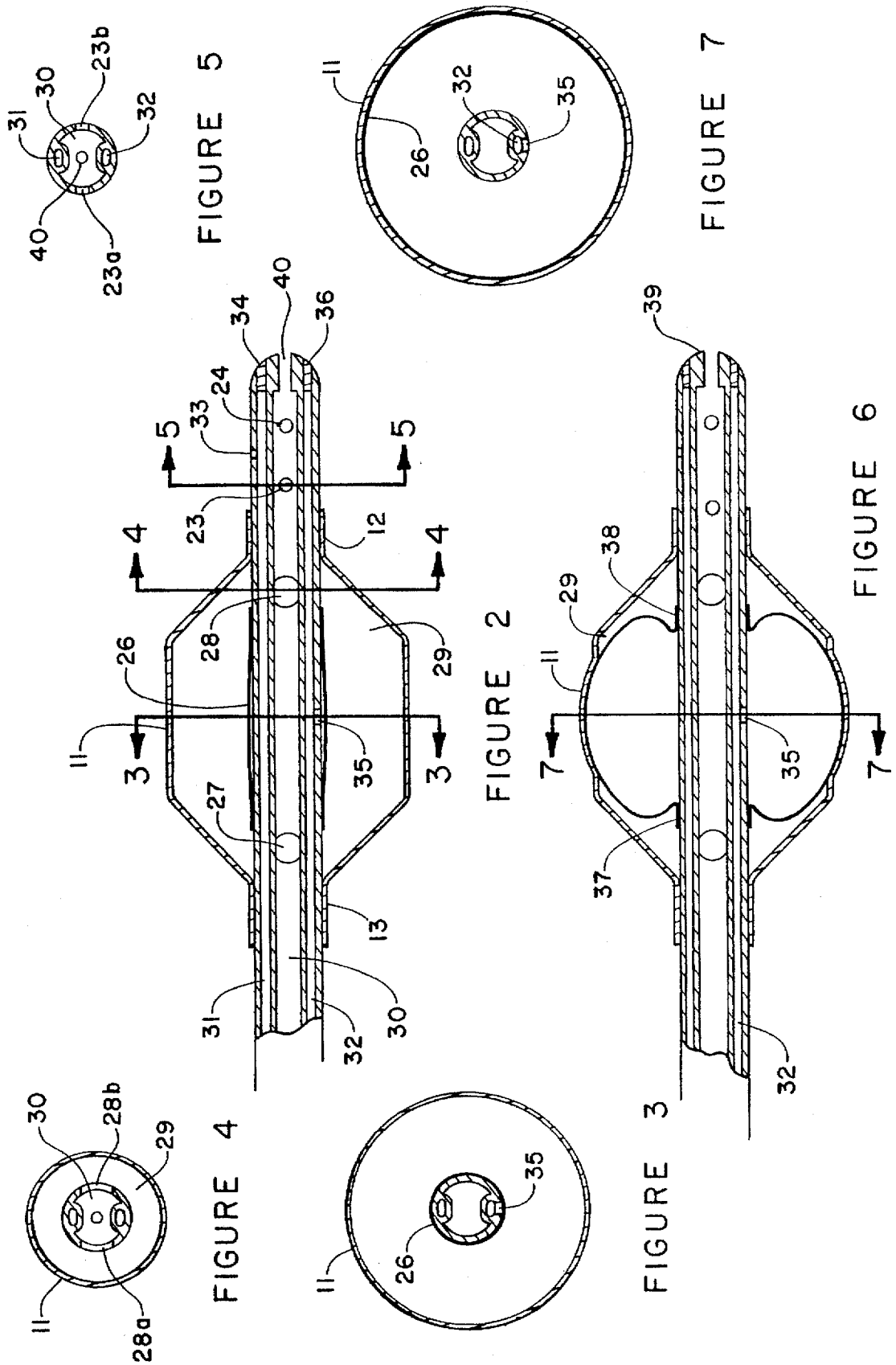

DUAL CONCENTRIC BALLOON CATHETER FOR RETROGRADE CARDIOPLEGIA PERFUSION

FIELD OF THE INVENTION

This invention relates to a temporary cannula for the delivery of a cardioplegia solution to the heart during cardiac surgery.

BACKGROUND OF THE INVENTION

It is common surgical practice to undertake cardiac surgery on patients with severe coronary artery disease, valve disease or for congenital deformations of the heart and its associated vessels. During the surgery, the surgeon typically arrests the heart by replacing its supply of oxygenated blood to the coronary circulation by a cold cardioplegia solution. The cardioplegia solution is frequently composed of a mixture of oxygenated blood and an electrolyte solution. The cardioplegia solution is often cooled to around before being perfused into the coronary circulation. Cardioplegia may be introduced to the coronary circulation through the coronary arteries via the coronary ostia (antegrade cardioplegia), or through the coronary veins via the coronary sinus (retrograde cardioplegia). Retrograde coronary flow has been shown to be particularly effective at myocardial preservation, especially in the presence of coronary artery disease. In most patients a combination of antegrade and retrograde cardioplegia is used.

Retrograde cardioplegia is routinely administered to the coronary sinus of the heart by means of a retrograde cardioplegia cannula. The cannula, which has a balloon near to its distal end, is introduced into the coronary sinus by insertion through the patient's right atrium. Following insertion through the atrium, the catheter is advanced until the tip enters the coronary sinus. The catheter is then advanced a few centimeters further in the coronary sinus. A balloon close to the distal tip of the catheter is then inflated. The balloon serves both to retain the cannula in place by gripping the periphery of the coronary sinus, and to prevent the infused cardioplegia solution from leaking from the end of the infusion catheter back into the right atrium.

Retrograde cardioplegia cannula are known in the art. Two techniques for inflating the balloon (or cuff) at the distal end of the catheter are used. In one type the balloon is inflated manually (after the catheter is placed in correct position) by the surgeon. A syringe which is connected to the catheter balloon by a narrow inflation lumen is used to inflate the balloon with air or liquid. In the second type the balloon is made to be self-inflating. In this latter arrangement the balloon is connected to the main flow lumen of the catheter, and a flow restriction distal to the balloon causes a sufficient back pressure build-up (in response to flow) to adequately inflate the balloon. The flow restriction distal to the balloon can take the form of one or several restrictive orifii.

Retrograde cardioplegia catheters are known in the art and are available commercially. Many surgeons use catheters with self inflating balloons. A similar number of surgeons prefer catheters with balloons that are manually inflatable.

Several companies market retrograde cardioplegia catheters with manually inflatable balloons (e.g. Medtronic-DLP supply a catheter model number 94115, and Research Medical, Inc. supply a catheter model number RC-014-MIBB). Catheters utilizing self inflating balloons were described by Buckberg in U.S. Pat. No. 5,021,045 and by Williams, Gronsman and Briscoe in U.S. Pat. No. 5,385,548. Medtronic-DLP and Research Medical, Inc. both supply catheters utilizing self-inflating balloons.

A catheter with a manually inflated balloon has the advantage that once the catheter is correctly positioned and the balloon is correctly inflated, the cannula is maintained in position and leakage between the catheter and the wall of the coronary sinus is eliminated. The difficulty of the manually inflated balloon catheter is that is quite difficult for the surgeon to accurately judge the correct level to which the elastic balloon is inflated. Under inflation results in the possibility of leakage of cardioplegia solution past the balloon, and the catheter may dislodge from the coronary sinus, especially if the heart is moved. Conversely, over inflation (either deliberate or accidental) may cause trauma to or rupture of the wall of the coronary sinus or other difficulties, including a breach of the balloon.

A catheter with a self-inflating balloon has several advantages. One is that the inflation of the balloon is automatic and is therefore a task that the surgeon does not have to perform. Another advantage is that the maximum internal pressure in the balloon is limited by the design of the catheter and the flow rate of cardioplegia solution thorough the cannula. Consequently over distention or rupture of the balloon and hence the coronary sinus is unlikely, especially if the pressure in the coronary sinus is being monitored. The major disadvantage of the catheter equipped with a self-inflating balloon is that when the infusion rate of cardioplegia solution ceases (or is slow) the internal pressure within the balloon drops to a low level. The balloon then becomes limp and the catheter is not properly retained in position in the coronary sinus. This disadvantage becomes apparent during manipulation of the heart when the catheter may dislodge. For example, when lifting and partial rotation of the heart to exposure the circumflex branch of the left coronary artery.

SUMMARY OF THE INVENTION

This invention is intended to provide the advantages of both types of catheter, while overcoming the individual disadvantages by utilizing a self-inflating balloon as well as a manually inflatable balloon. In the preferred embodiment the self-inflating balloon is located concentrically around the manually inflatable balloon. Concentric placement is desirable because the portion of the coronary sinus in which the catheter is placed is generally too short to allow two balloons to be placed in tandem on the catheter.

In a preferred form, the invention comprises a cardioplegia catheter for use in cardiac surgery comprising an elongate flexible tube defining at least two, and preferably three, lumina having a distal end for dwelling in the coronary sinus of the patient, a cardioplegia connector near the proximal end of the tube for selectively introducing cardioplegia into the first lumen and, through the first lumen, into a first expandable balloon encompassing a portion of the tube near the distal end of the tube and to the exterior of the tube at the distal end for directing cardioplegia into the coronary sinus of the patient and expanding the first expandable balloon. The invention may also comprise a fluid pressure connector for selectively applying fluid into the second lumen of the tube and a second expandable balloon encompassing a portion of the tube in fluid communication with the interior of the second balloon for applying fluid pressure for selectively inflating said balloon to a desired pressure. The second balloon may be concentric with and inside the first balloon. The tube may define a third lumen through the length thereof and a fluid passage from the third lumen opening into the coronary sinus of the patent, when the catheter is in use a pressure sensing connector for sensing the pressure in the patient's coronary sinus through the third lumen.

BRIEF DESCRIPTION OF THE DRAWINGS

FIG. 2 shows a part cross-sectional view of the distal end of the catheter with the inner balloon deflated.

FIG. 3 shows a part cross-sectional view of the catheter taken along line 3—3 AA of FIG. 2.

FIG. 4 shows a part cross-sectional view of the catheter taken along line 4—4 of FIG. 2.

FIG. 5 shows a part cross-sectional view near the distal end of the catheter taken along line 5—5 of FIG. 2.

FIG. 6 shows a part cross-sectional view of the distal end of the catheter with the inner balloon inflated.

FIG. 7 shows a part cross-sectional view of the catheter taken along line 7—7 of FIG. 6.

DESCRIPTION OF THE PREFERRED EMBODIMENT

Figure 1:
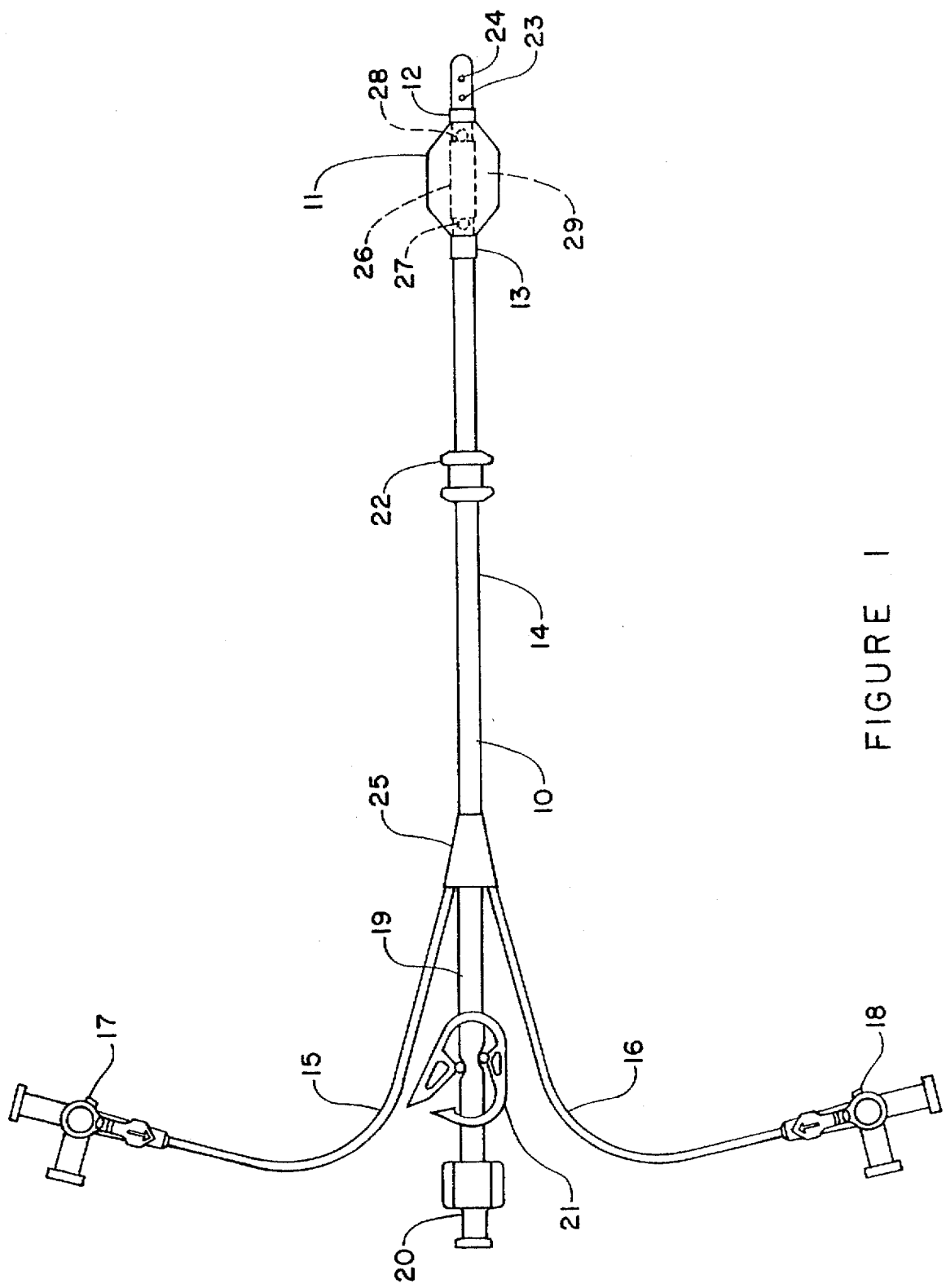
FIG. 1 shows a side elevation of the dual concentric balloon retrograde cardioplegia catheter.

Reference is made to the drawings wherein like numerals refer to like elements for a detailed description of the preferred embodiment of the invention. It will be understood that it is the overall combination of elements that constitutes the invention, as set forth in the claims, and that individual elements may vary considerably. Preferred dimensions are provided, but these are not critical. Preferred materials are disclosed, but the various elements may be made of alternative biologically compatible materials.

Referring now to FIG. 1, the catheter 10 has an outer self-inflating balloon 11, attached near the distal end of a three lumen extruded plastic or silicone elastomer tube 14 of approximately 3/16 outside diameter at points 12, 13. A pressure monitoring line 15, and inner balloon inflating line 16 are attached to inlet tube 19 and three lumen tube 14 at junction 25. Pressure monitoring line 15 and balloon inflating line 16 are terminated by stopcocks 17, 18 respectively. Inlet tubing 19 is terminated by a Luer-lock female connector 20, and has a pinch clamp 21 that allows inlet tube 19 to be temporarily occluded. Moveable hub 22, which may be slid along tube 14, allows the surgeon to retain the catheter in position by means of a ligature. At the distal end of the catheter are apertures (including 23, 24) through which the cardioplegia solution flows from the catheter into patient's coronary sinus.

Within the self inflating balloon 11, lies a manually inflatable cuff 26. Fluid path feed holes 27, 28, connect the main passage of tube 14 to the space 29 between self inflating balloon 11 and manually inflatable cuff 26.

This arrangement is made clearer by reference to the FIGS. 2 and 3 which show cuff 26 in the uninflated position and FIGS. 6 and 7 which show cuff 26 in the inflated position. Reference is also made in the following discussion to FIGS. 4 and 5.

Triple lumen delivery tube 14 has one major lumen 30, and two minor lumen 31, 32. Pressure monitoring lumen 31 is connected to pressure monitoring line 15 at junction 25, and to side hole 33 near its distal end. Lumen 31 is terminated by a plug 34 at its distal end. The third lumen, 32, of delivery tube 14 communicates to the inner surface of inflatable cuff 26 by means of side hole 35 in the outer wall of tube 14. Lumen 32 is terminated by a plug 36 at its distal end. Inflatable cuff 26 is fixed by fluid tight means to inlet tube 14 at 37, 38, such that the introduction of air or liquid via line 16, lumen 32, and side hole 35, causes inflatable cuff 26 to expand. Tube 14 is terminated at its distal end by a rounded smooth tip 39, containing a small central hole 40. Through holes 27, 28, provide a liquid path between passage 30 and space 29 (as shown in FIG. 4). Near to the distal end of the catheter are a series of holes, a pair of holes 23a and 23B and another pair of holes at the location indicated at 24 on opposite sides of the lumen, and an end hole 40, through which the cardioplegia solution flows from the catheter into patient's coronary sinus. Typically a pair of holes located as indicated at 23 and a pair of holes located as indicated at 24 and an end hole 40 are provided. The tube 14 is so constructed and configured as to provide a combined passage area of holes 23, 24 and 40 sufficient to cause sufficient pressure differential during cardioplegia infusion to adequately inflate the self inflating balloon. These holes are typically about 0.035" diameter. The embodiment illustrated in FIGS. 2 defines four balloon apertures, a pair of apertures at the location indicated at 27, and a pair of apertures at the location indicated at 28. More or less apertures may, however, be used. The number and size of the apertures will control the speed at which the balloon will fill, and the mechanical robustness of the catheter. Clearly, apertures of large area will allow fast inflation of the balloon, but might compromise the stiffness of the catheter, resulting in a the possibility of kinking within the confines of the balloon. The various materials are suitable for use for the catheter body. When the catheter is first introduced the material will be at or near room temperature, but with the infusion of the cardioplegia solution, the temperature will fall to that of the solution (typically about 4° C.). Whereas, both polyvinyl chloride (PVC) and silicone elastomer have been used for retrograde cardioplegia cannula, polyurethane has improved low temperature flexibility as compared to PVC.

The outer balloon, which is about 0.7" diameter, may be of polyurethane, and fabricated either by blow molding or by dipping, while the inner cuff may be of silicone rubber. The used of different materials for the two balloons can be advantageous to prevent the inner balloon from sticking to the outer balloon. The sensing aperture 33, is typically of the same cross-sectional area as is lumen 31.

Method of Use

The catheter of the present invention may be introduced into the coronary sinus via the right atrium either using a guide wire, or using a curved or malleable introducer placed in the major lumen of the catheter. In either case, a purse string ligature is first placed in the wall of the right atrium, and a small central incision made through the atrial wall. The catheter containing the introducer is inserted through the incision and the tip of the catheter placed into the coronary sinus. The catheter is then advanced a few centimeters. Depending upon the surgeons preference, the ligature is then tightened around the body of the catheter, the introducer removed, and the manually inflated balloon partially or fully inflated. Alternatively, the surgeon may desire to leave the manual balloon deflated until it is necessary to manipulate the heart. During the infusion of cardioplegia solution, the self-inflating outer balloon will become pressurized, and following the cessation of cardioplegia infusion, the manually inflatable balloon may be inflated. Should the surgeon so desire, the manually inflated balloon may the partially filled initially, sufficient to stabilize the catheter. Perfusion of cardioplegia solution will then further inflate the self-inflating balloon thus preventing leakage past the outer balloon. The degree to which the inner balloon will influence the outer balloon will depend upon the degree to which the inner balloon was inflated, whether it was inflated with air or liquid, and the resilience of the outer balloon. Thus by having both balloon types available on one catheter, the surgeon has more control over catheter stability and reliable delivery of retrograde cardioplegia solution into the coronary sinus of the heart.

Industrial Application

This invention finds application in the surgical instrument industry and in the practice of human and veterinary medicine.

What is claimed is:

1. A cardioplegia catheter for use in cardiac surgery comprising, in combination:

an elongate flexible tube of biocompatible material having a length and a proximal end for, in use, dwelling outside the patient's heart and a distal end for, in use, dwelling in the coronary sinus of the patient, said tube defining at least first and second lumina lengthwise there through;

a cardioplegia connector proximate the proximal end of the tube for selectively introducing cardioplegia into the first lumen;

a first expandable balloon having an exterior and an interior encompassing a portion of the tube proximate the distal end of the tube, the tube being so constructed and configured as to define a first passage from the first lumen to the exterior of the tube proximate the distal end thereof for directing cardioplegia into the coronary sinus of the patient and a second passage from the first lumen in fluid communication with the interior of the first expandable balloon for directing cardioplegia into the said first balloon for expanding the same;

a fluid pressure connector proximate the proximal end of the tube for selectively applying fluid into the second lumen of the tube; and a second expandable balloon having an exterior and an interior encompassing a portion of the tube inside of the first expandable balloon, the tube being so constructed and configured as to define a third passage from the second lumen in fluid communication with the interior of the second balloon for applying fluid pressure from the fluid pressure connector to the interior of the second balloon for selectively inflating said balloon to a desired pressure.

2. The cardioplegia catheter of claim 1 wherein:

the tube is so constructed and configured as to define a third lumen through the length thereof and a fluid passage from the third lumen opening into the coronary sinus of the patent, when the catheter is in use; and further comprising a pressure sensing connector proximate the proximal end of the catheter for sensing the pressure in the patient's coronary sinus through the third lumen.

3. A cardioplegia catheter for use in cardiac surgery comprising, in combination:

an elongate flexible tube of biocompatible material having a length and a proximal end for, in use, dwelling outside the patient's heart and a distal end for, in use, dwelling in the coronary sinus of the patient, said tube defining at least first and second lumina lengthwise there through;

a cardioplegia connector proximate the proximal end of the tube for selectively introducing cardioplegia into the first lumen;

a first expandable balloon having an exterior and an interior encompassing a portion of the tube proximate the distal end of the tube, the tube being so constructed and configured as to define a first passage from the first lumen to the exterior of the tube proximate the distal end thereof for directing cardioplegia into the coronary sinus of the patient and a second passage from the first lumen in fluid communication with the interior of the first expandable balloon for directing cardioplegia into the said first balloon for expanding the same;

a fluid pressure connector proximate the proximal end of the tube for selectively applying fluid into the second lumen of the tube; and a second expandable balloon having an exterior and an interior encompassing a portion of the tube, the tube being so constructed and configured as to define a third passage from the second lumen in fluid communication with the interior of the second balloon for applying fluid pressure from the fluid pressure connector to the interior of the second balloon for selectively inflating said balloon to a desired pressure.

4. The cardioplegia catheter of claim 3 wherein:

the tube is so constructed and configured as to define a third lumen through the length thereof and a fluid passage from the third lumen opening into the coronary sinus of the patent, when the catheter is in use; and further comprising a pressure sensing connector proximate the proximal end of the catheter for sensing the pressure in the patient's coronary sinus through the third lumen.

5. A multiple lumen catheter comprising a tube having a length and proximal and distal ends that defines at least first and second lumina, first and second balloons secured on said tube proximate the distal end thereof, said tube defining a fluid passage from the first lumen to the first balloon and a second fluid passage from the second lumen to the second balloon, the tube being so constructed as to define a fluid flow path proximate the distal end of the tube from only one of said lumen to the exterior of the tube for introducing fluid from the catheter into a balloon and for passing fluid from the distal end of the tube.

6. A multiple lumen catheter comprising a tube having a length and proximal and distal ends that defines at least first and second lumina, first and second balloons secured concentrically on said tube proximate the distal end thereof, said tube defining a fluid passage from the first lumen to the first balloon and a second fluid passage from the second lumen to the second balloon, the tube being so constructed as to define a fluid flow path proximate the distal end of the tube from only one of said lumen to the exterior of the tube for introducing fluid from the catheter into a balloon and for passing fluid from the distal end of the tube.

7. The catheter of claim 6 wherein the second balloon is inside the first balloon and the tube defines a passage from the first lumen to the exterior of the tube.

* * * * *